United States Patent [19]

Shirazi

[11] Patent Number: 5,492,832
[45] Date of Patent: Feb. 20, 1996

[54] VERY LOW TEMPERATURE ASHING (VLTA)

[76] Inventor: Ahmed R. Shirazi, Liedstrandsgatan 6, S-416 58 Göteborg, Sweden

[21] Appl. No.: 190,100
[22] PCT Filed: Jun. 16, 1992
[86] PCT No.: PCT/SE92/00428
§ 371 Date: Feb. 2, 1994
§ 102(e) Date: Feb. 2, 1994
[87] PCT Pub. No.: WO93/03363
PCT Pub. Date: Feb. 18, 1993

[30] Foreign Application Priority Data

Aug. 9, 1991 [SE] Sweden ................................. 9102320

[51] Int. Cl.⁶ ............................. G01N 5/04; G01N 25/26
[52] U.S. Cl. ................ 439/55; 436/160; 436/175; 436/181; 436/182; 436/173; 422/186.04; 422/186.05; 431/8; 431/10; 110/342; 110/347; 588/205
[58] Field of Search .................. 110/210, 222, 110/232, 245, 259, 236, 342, 347; 106/405, 407; 588/205, 828; 134/1, 38; 422/186.04, 186.05; 436/156, 160, 55, 174, 175, 181, 182, 173; 73/23.31; 431/8, 10

[56] References Cited

U.S. PATENT DOCUMENTS 4,234,315  11/1980  Scott .......................... 436/160
4,474,621  10/1984  Saccocio et al. ............... 134/1
4,532,219  7/1985   Hagen et al. .................. 436/155
4,799,799  1/1989   Sapko et al. .................. 356/446
4,824,790  4/1989   Carangelo et al. ............. 436/157
5,204,270  4/1993   LaCount ....................... 436/157

*Primary Examiner*—David A. Redding
*Attorney, Agent, or Firm*—Samuels, Gauthier & Stevens

[57] ABSTRACT

A method and system for Very Low Temperature Ashing (VLTA). In one embodiment, there is provided a method of ashing solid fuel or combusted or partly combusted fuel or any organic and inorganic matrix which contains minerals in a furnace with a partial pressure less than atmospheric pressure including the step of mixing of oxygen and helium with a total pressure less than the atmospheric pressure and producing a plasma in which the mineral components in the samples are not being affected essentially, wherein the proportion of the gas mixture achieve a surface temperature not exceeding 150° C. on the sample. In an alternative embodiment, there is provided a method of ashing solid fuel or combusted or partly combusted fuel or any organic and inorganic matrix which contains minerals in a surface with a plasma including the step of regulating the proportion between oxygen and helium by a reduction of oxygen content, wherein the surface temperature shall not exceed 150° C. and the temperature being controlled during the entire ashing procedure.

15 Claims, 8 Drawing Sheets

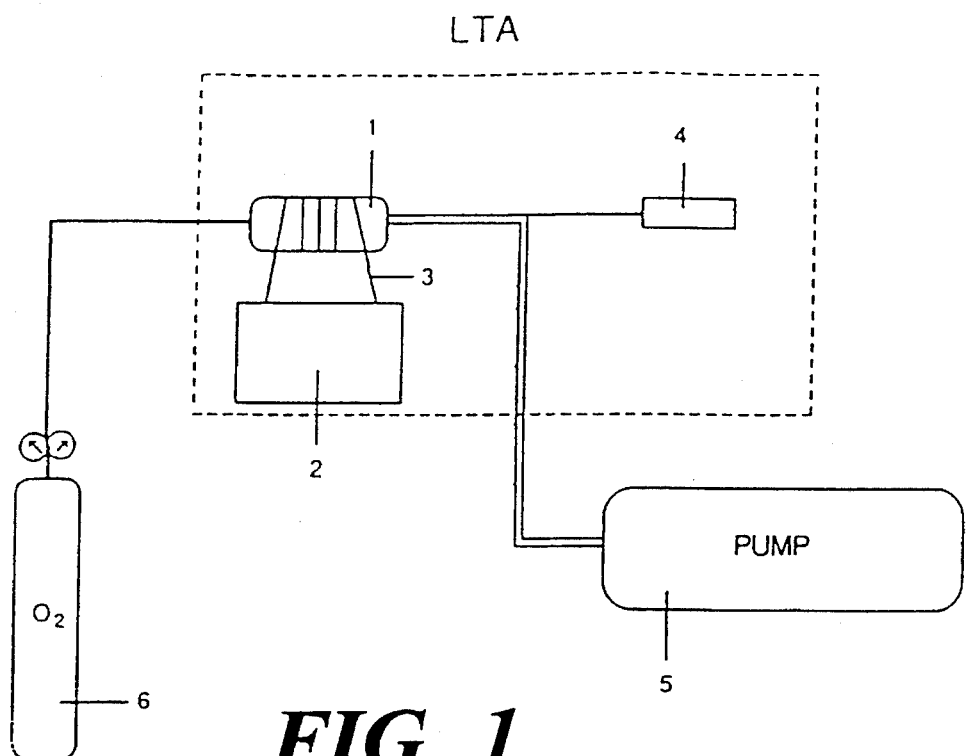
FIG. 1
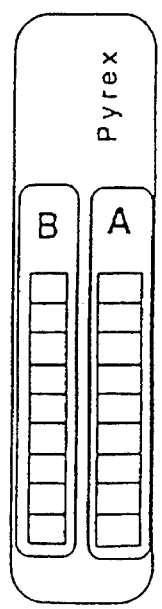
FIG. 2A FIG. 2B FIG. 2C FIG. 2D

VERY LOW TEMPERATURE ASHING (VLTA)

BACKGROUND OF THE INVENTION

The invention pertains to the field of ashing of solid fuels or combusted or partly combusted fuels, or any organic and inorganic matrix which contains minerals, e.g. oil and human blood, at low to very low temperature. All solid fuels, whether they consist of renewal biomass, fossil fuels such as coal and peat or fuels in gas phase or liquid phase, am based on carbon, hydrogen, oxygen and nitrogen. In addition these elements, solid fuels also contain minerals such as sulphur, silica and metals, often connected to oxygen. Minerals with the uncombusted matter constitute the ash, which consists of various oxides, sulphates and silicates as well as other chemical compounds. Table Ia shows an example of the composition of an ash from coal obtained by chemical analysis. Table Ib show an example of the most common minerals in coal.

TABLE Ia

| | |
|---|---|
| $SiO_2$ | 25–50% |
| $Al_2O_3$ | 10–40% |
| $Fe_2O_3$ | 5–30% |
| $CaO$ | 1–15% |
| $MgO$ | 0.5–5% |
| $TiO_2$ | 0.5–3% |
| $Na_2O + K_2O$ | 1–4% |
| $SO_3$ | 0.1–10% |

TABLE Ib

Silicates (Quartz $SiO_2$, Feldspar (K, Na)$(AlSi_3O_8)$, $CaAl_2Si_2O_8$)
Clayminerals (Illite $K_{1-1.5}Al_4(Si_{7-6.5}Al_{1-1.5}O_{20})(OH)_4$,
Kaolinite $Al_4(Si_4O_{10})(OH)_8$,
Montmorillonite (½ Ca, Na)$_{0.7}$ (Al, Mg, Fe)$_4$
$((Si, Al)_8O_{20})(OH)_4 \cdot n\ H_2O)$
Sulphates (Anhydrite $CaSO_4$, Barite $BaSO_4$)
Sulphides (Pyrite $FeS_2$, Marcasite $FeS_2$, Sphalerite ZnS)
Elemental Sulphur $S_8$
Carbonates (Calcite $CaCO_3$, Siderite $FeCO_3$)

On combustion ashes are formed along with the gases, which principally are carbon monooxide and carbon dioxide. Furthermore, nitrogen oxides ($NO, N_2O, NO_2$) are formed by oxidation of nitrogen in the fuel or in the air. Sulphur dioxide and sulphur trioxide are also present in the gases. The sulphur oxides are formed by the oxidation of sulphur in coal, which is present in three modes, namely organic sulphur, sulphides and sulphates. The sulphides and sulphates are counted as mineral matter in the fuels.

It is desirable to choose fuel with low sulphur content, whereby the emission of sulphur oxides decreases.

It is seen from the foregoing that it is important that the selection of the fuel is not based simply on its specific heat, but also on a knowledge of the composition of the mineral matter.

The performance of chemical analyses on the ash are well known and the customary procedure is first to ash the sample, which means that the organic matter in the fuel oxidizes at high temperature in the presence of oxygen (air). The obtained ash can be analyzed in a relevant manner.

The ash can also be mounted in the mounting material and a cross-section of the ash can be analyzed using an electron microscope. In this case it is possible to analyze the ash by x-ray methods.

In order to perform X-ray analysis the ashing of the samples should have proceeded as long as possible before the mounting of the ashes is carried out.

The compounds in the sample usually oxidize at high temperature and high oxygen content. For example, iron which usually exists as $Fe^{2+}$ compounds, is oxidized to $Fe_2O_3$. Iron sulphides and copper sulphides oxidize to sulphates. Calcium oxide transforms to calcium sulphate by reaction with $SO_2$, which originates from the just mentioned sulphides. Consequently, the original composition of the mineral matter in the fuel is not reflected by the results of the chemical analysis.

To be able to study the ash more thoroughly, the phase composition of the minerals is essential. Table Ib show an example of the minerals which usually occur in solid fuels.

It is important to find methods in which ashing of the fuel sample can be performed without phase modifications or losses of the minerals at as low a temperature as possible. One of these methods is Low Temperature. Ashing (LTA) which will be described below.

Since 1965 it has been known (Gluskoter, Fuel, 44, 285–291) that by applying an radio frequency field to a gas atmosphere containing 100% oxygen a plasma is obtained, that is a gas containing electrically conductive ions, and this plasma has the ability to oxidize carbon bound to other organic and inorganic material.

SUMMARY OF THE INVENTION

The ashing of the solid fuels and the characterization of the mineral matter in these fuels have been of great importance for a long time. Low Temperature Ashing (LTA) is a method to ash solid fuels and it has been known since 1965. The problem has been that the ashing temperature could not be measured and consequently the ashing process could not be controlled.

This invention called Very Low Temperature Ashing (VLTA) refers to obtaining an ashing of solid fuels (or ashes with uncombusted material) in such a way that no modifications, losses or damages of the original phases, especially sulphide minerals, occurs. In order to achieve this and to decrease and control the ashing temperature, the oxygen has been blended with helium in different quantities. The gas which is formed during the oxidation of the samples was analyzed simultaneously especially regarding the $SO_2$.

According to the invention, the ashing temperature and the formation of $SO_2$ can be controlled to low levels by regulating of the helium/oxygen mixture.

It was surprisingly established that the ashing according to the invention occurs selectively with regard to the carbon in the samples. The expression "selective" refers to the fact that merely or principally the carbon in the samples oxidizes, while the sulphur compounds are unaffected in the samples. This selective oxidation occurs at an ashing temperature interval between 60°–70° C. for all coal samples or solid fuels, regardless of the ranks (calorific values) of the samples. Accordingly, the present invention provides a method of ashing solid fuel or combusted or partly combusted fuel or any organic and inorganic matrix which contains minerals, in a furnace with a partial pressure less than atmospheric pressure comprising the steps of mixing oxygen and helium with a total pressure less than the atmospheric pressure and producing a plasma in which the mineral components in the samples are not being affected essentially, wherein the portion of the gas mixtures achieves a surface temperature not exceeding 150° C. on the sample.

In an alternative embodiment of the present invention, there is provided a method of ashing solid fuel or combusted or partly combusted fuel or any organic and inorganic matrix which contains minerals, in a furnace with a plasma comprising the steps of regulating a proportion between oxygen and helium by a reduction of oxygen content, wherein the surface temperature shall not exceed 150° C. and the temperature being controlled during the entire ashing procedure.

BRIEF DESCRIPTION OF THE DRAWINGS

FIG. 1 shows a schematic of equipment used for low temperature ashing in accordance with the present invention;

FIGS. 2a–d show ashing temperature thermographic indicators utilized in accordance with the present invention;

DETAILED DESCRIPTION OF THE ILLUSTRATED EMBODIMENTS

Figure 3:
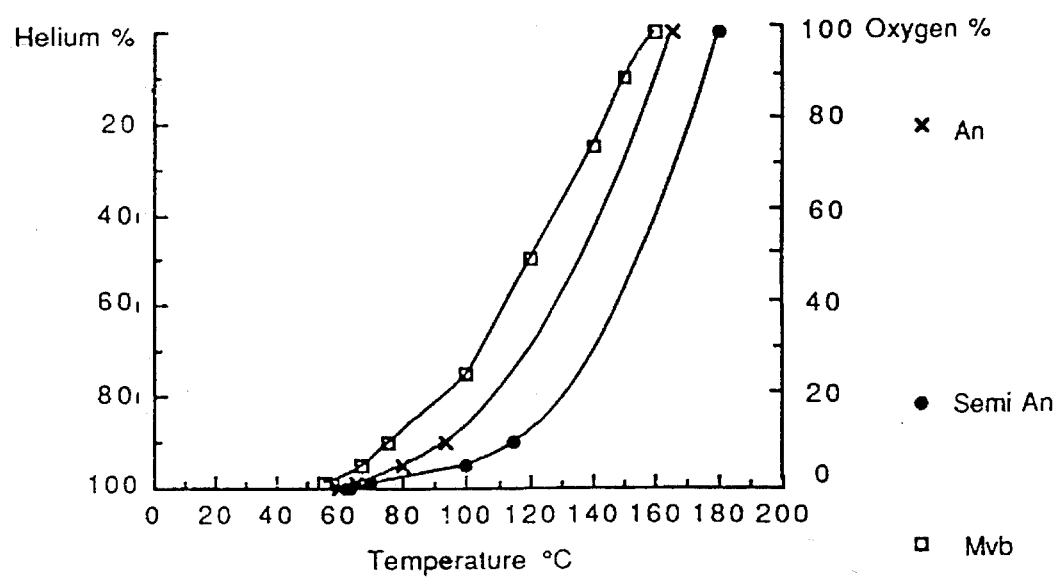
FIG. 3 shows the graphical relationship between oxygen content and ashing temperature for coal samples in accordance with the present invention.

FIG. 1 show schematically equipment for low temperature ashing with oxidation chambers (1), radio frequency (RF) generator (2), RF-coil (3), vacuum gauge (4), vacuum pump (5) and oxygen container (6). According to the manufacturer's (LFE Corporation) description, 1–2 g of a coal sample (fuel sample) have been spread on glass boats and placed in the low pressure chambers (1).

The vacuum pump (5) adjusts a vacuum equivalent to 0.1 mbar in the low pressure chambers (1), which contain small proportions of oxygen from the oxygen container (6). By starting the generator (2) the plasma forms in the oxidation chambers (1).

The following results have been obtained according to the manufacturer's description; The experiment began with 20 ml/min 100% oxygen (table II), and the plasma struck with 50W effect. Since the ashing temperature increases with increasing gas flow and increasing RF-effect, a gas flow equivalent to 20 ml/min and a RF-effect of 50W was chosen, since these values are the lowest possible experimental choices and therefore best suited for this study.

After 24 hours of ashing it was observed that on one hand the temperature reached 250°–300° C. (see temperature measurement below), and on the other hand the coal sample was oxidized intensely on the surface, but the sample was almost intact in the inside.

Thus the temperature inside the LTA has not been possible to measure or control, the oxidation temperature was varied for different samples with different calorific values.

Figure 4A:
FIGS. 4a–4d respectively show a cross-section of a grain of an iron sulfide, and the distributions of the elements FeSO.

The analyses of the ashes by electron microscope shows that the sulphide minerals have been oxidized to sulphates FIG. 4a shows a cross-section of a grain of an iron sulphide.

Figure 4B:
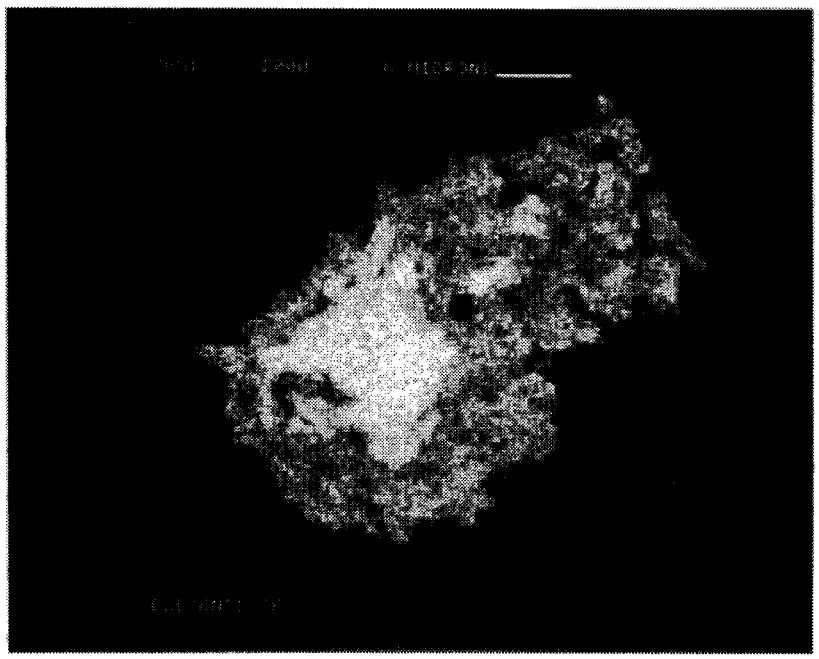
Figure 4C:
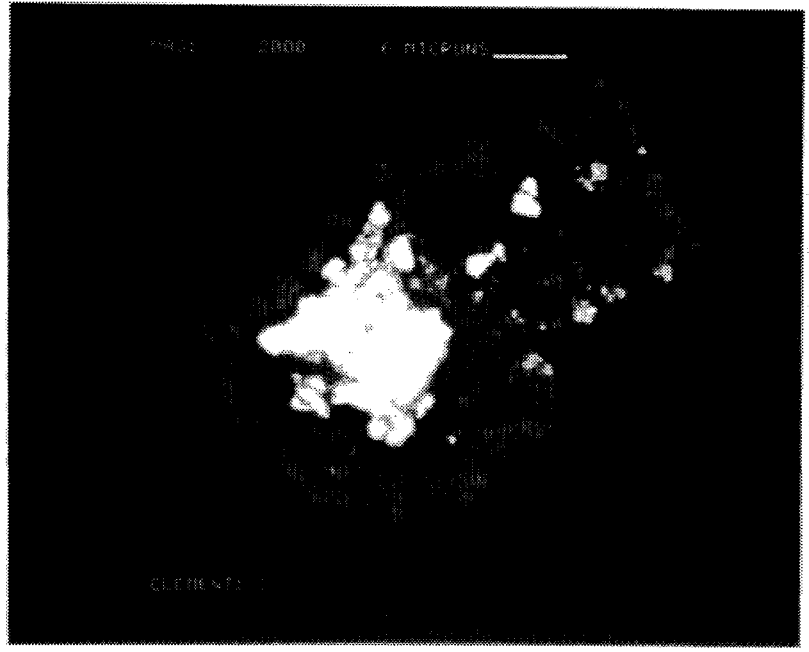
Figure 4D:
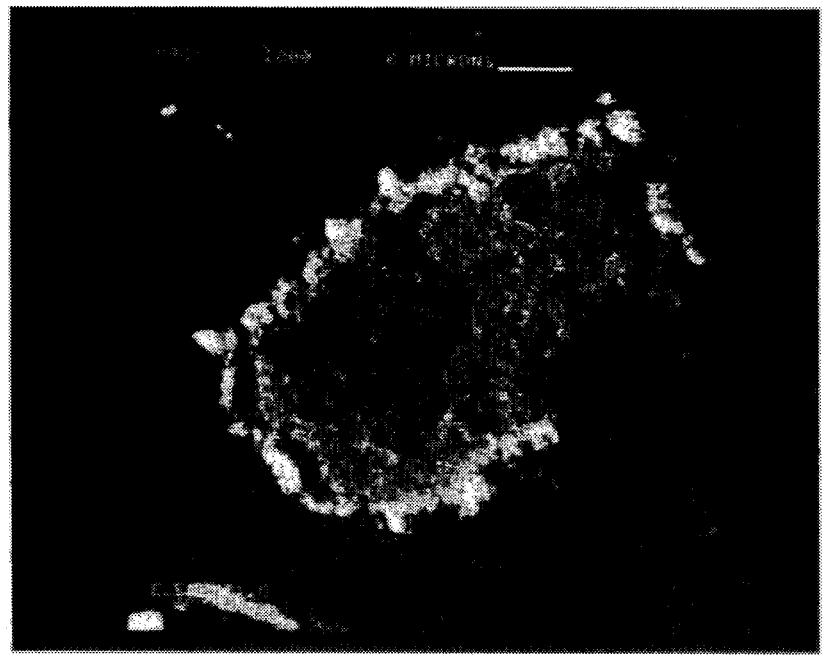

In the FIGS. 4b–4d respectively show the distributions of the elements Fe, S and O are presented, showing that some parts of the grain have been sulphated during the ashing process, which means that some of the sulphur from the grain has been lost as $SO_2$. As mentioned, the process took place in 100% oxygen and at a low pressure ($10^{-1}$ mbar).

In general, 1–2 g coal or biomass sample is oxidized during a period of 12–48 hours. It has been seen experimentally that under these conditions the surface temperatures are too high (250°–300° C.) for some coal samples, and the carbon as well as iron sulphides, copper sulphides and elemental sulphur also oxidize.

It can be concluded from the electron microscope analysis and from Table III that the ashing and enrichment of the minerals in fuels cannot be performed in LTA and with the manufacturer's (LFE Corporation) description, since some of the minerals are lost or modified. It appears from this that the ordinary LTA procedure oxidizes the mineral matter and some minerals are also lost during an ashing. This casts doubt the generally accepted advantages of LTA as a method, since the experimental parameters (gas flow, RF-effect) are the lowest possible. It appears from this that the LTA is not the best method of ashing the fuel samples without losses or modifications.

The present invention (Very Low Temperature Ashing, VLTA) circumvents these difficulties and comprises a method of ashing biomass as well as fossil fuels without losses or modifications of the minerals.

LTA is not appropriate for obtaining exact information about composition of the mineral matter in fuel prior to the combustion, since the iron sulphides oxidize to sulphates or are lost as $SO_2$ in the process.

It may be surprising that according to the invention the oxidation of the carbon occurs not solely at a very low temperature, but also selectively in regard to the carbon in the fuel, in an ashing atmosphere (oxygen) still at low pressure, blended with helium in certain proportions. The expression "selective" suggests that mainly the carbon in the fuel is oxidized, while the sulphur compounds are unaffected in the fuel. This procedure provides a more efficient plasma as well as keeping the oxidation temperature low.

The goal of the invention is to produce an ashing of the mentioned material in this way. It is described in detail in the following text.

Figure 6:
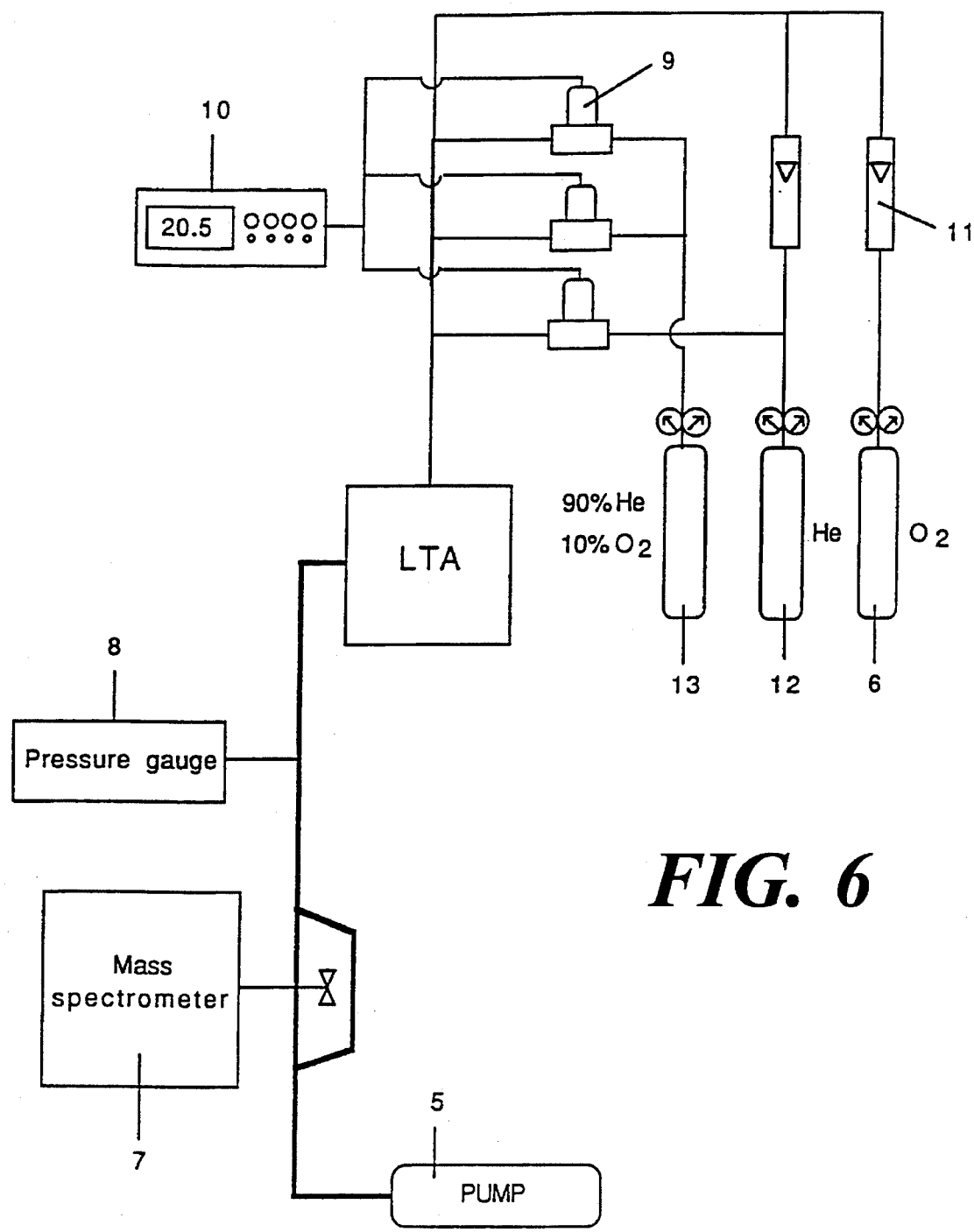
FIG. 6 shows a schematic of an exemplary set-up of the very low temperature ashing system in accordance with the present invention.

Very Low Temperature Ashing (VLTA) is a method in which ashing of fuel samples occurs at a low to very low temperature and in a controlled manner as is described with reference to FIGS. 3 and 6. FIG. 6 shows a schematic of the experimental set-up of VLTA with mass spectrometer (7), vacuum gauge (8), mass flow controllers (9) with attached control unit (10), flow meters (11), helium container (12), oxygen container (6) and container with a mixture of 90% helium and 10% oxygen (13).

By controlling the oxygen content in the plasma the oxidation temperature can be controlled and phase modifications of the minerals in the sample can be prevented as is described with reference to FIGS. 4a–4d and 5a–5d. FIG. 3 shows the relationship between oxygen content and ashing temperature for coal samples Antracite (An), Semiantracite (SemiAn) and Medium-volatile bituminous (Mvb).

In order to measure the ashing temperature thermographic indicators were used. These indicators show the highest oxidation temperature reached during the ashing process by a colour change from silver-white to black. These indicators were enclosed in Pyrex ampoules to protect the indicators from burning in the atmosphere of the chambers (1). The indicators were then placed in the sample boat and covered by coal as is shown in FIGS. 2a–2d.

The experiment was repeated with the same coal sample (and same gas flow and RF-effect) and a gas mixture consisting of 1% $O_2$ and 99% He at low pressure flowing into the chambers.

It was established that the temperature was considerably lower, 65°–70° C., and the sample was oxidized homogeneously. It has been seen experimentally that the proportion between oxygen and helium must be adjusted for different coal samples to obtain this very low (60°–70° C.) ashing temperature as is shown in the graph of FIG. 3. At this low ashing temperature the oxidation of the samples occurs selectively.

Figure 5A:
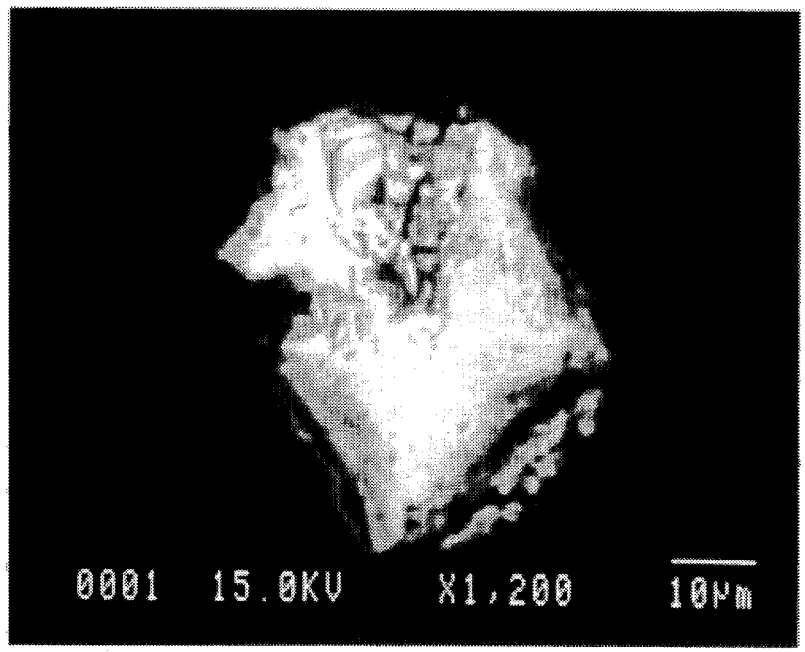
FIGS. 5a–5d respectively show a cross-section of an iron sulfide grain, and the distributions of the elements FeSO.
Figure 5B:
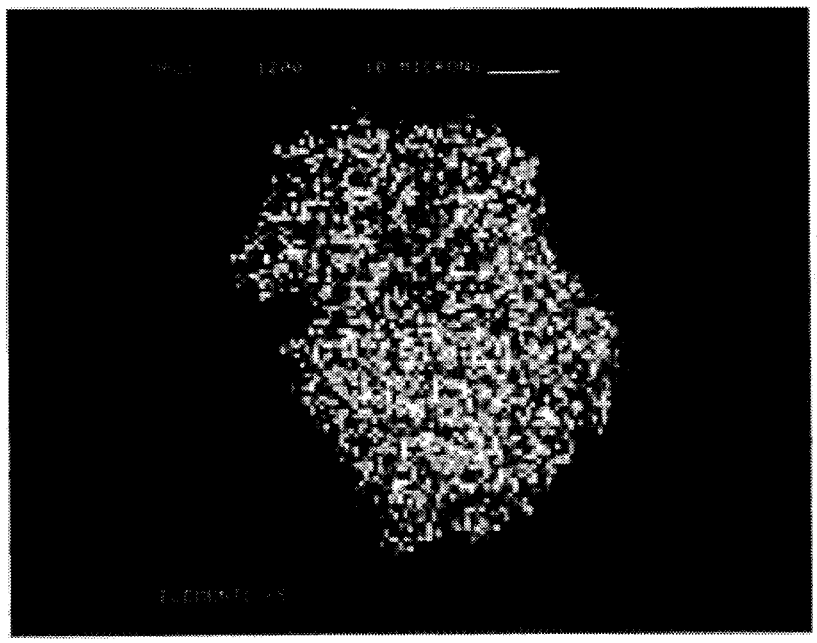
Figure 5C:
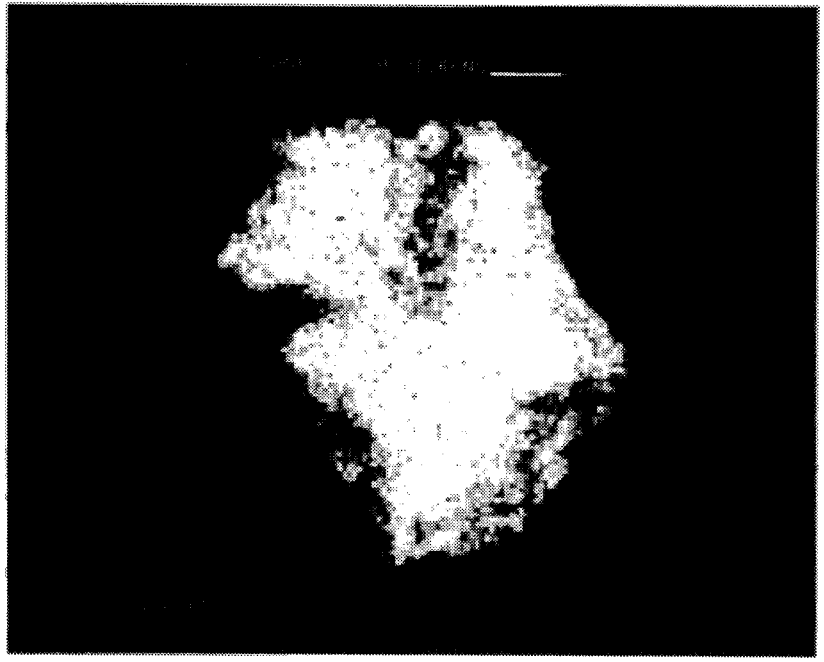
Figure 5D:

The electron microscopic analysis showed that the iron sulphides were unaffected (FIG. 5a). FIG. 5 show a cross-section of an iron sulphide grain. The distributions of the elements Fe, S and O are shown in the FIG. 5b–5d. It can be seen that the iron sulphide is unaffected.

It can be concluded from this that an ashing without any phase modifications or losses can only be obtained by VLTA.

Figure 7:
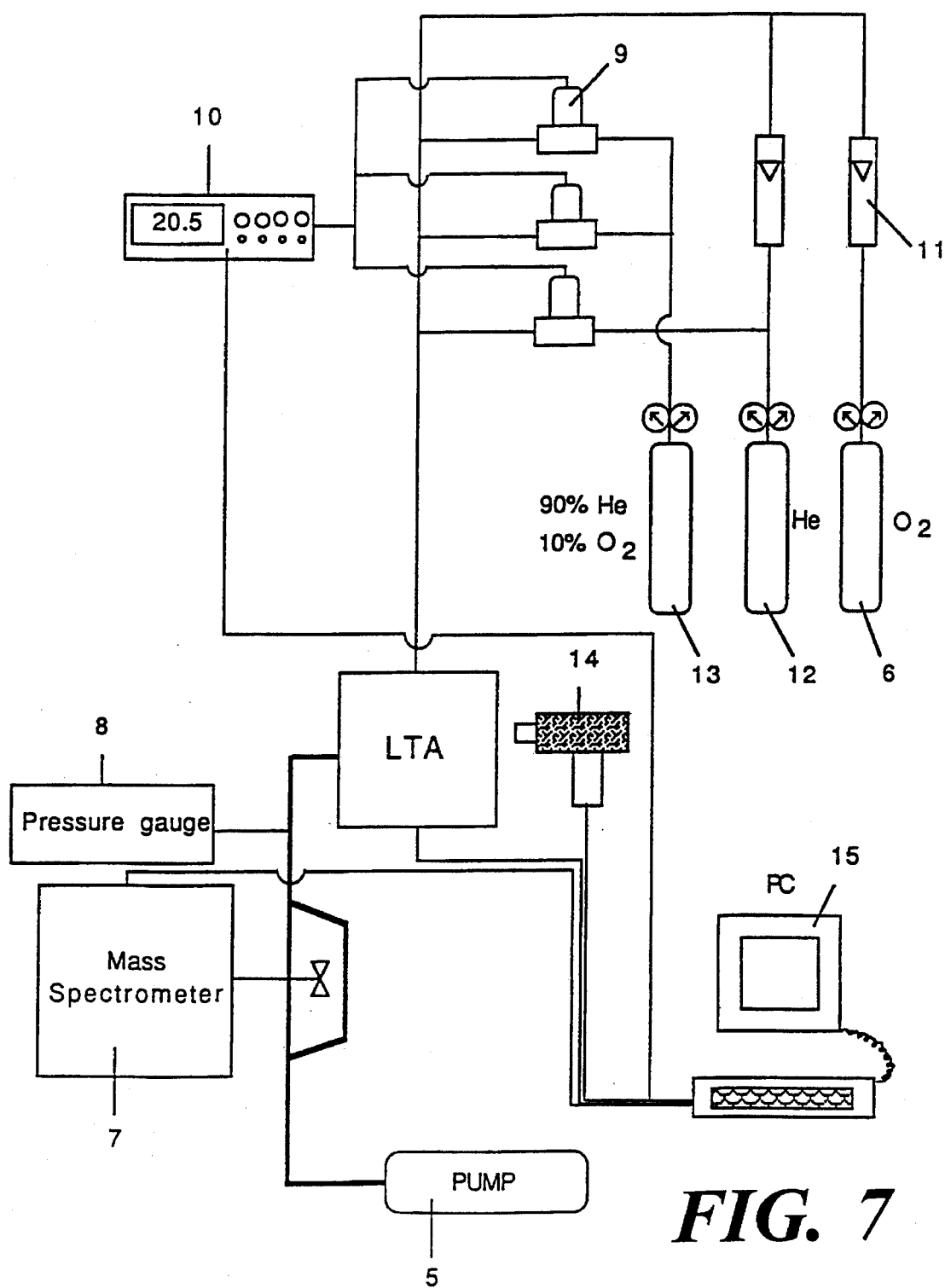
FIG. 7 shows an exemplary schematic of an alternative set-up of the very low temperature ashing system in accordance with the present invention.

The temperature measurement in VLTA can also be performed with an IR-detector (14) as shown in FIG. 7 which can be placed just outside the oxidation chambers (1), which permits tile IR-radition to pass. The VLTA process can be automated with a computer (15) which controls the ashing temperature and the $SO_2$ in the off-gas by adjusting the gas flow and RF-effect. In this way an efficient selective oxidation can be performed during tile entire ashing process (see below).

Six coal samples of different ranks and sulphur content were chosen for this investigation. The choice was made so that they cover almost all the ASTM-ranks. A peat sample was also ashed to get a better understanding of the applicability of the technique. The samples were ashed in different gas mixtures of helium and oxygen, and the off-gas was analyzed simultaneously with regard to $SO_2$. This analysis was performed with a quadropule mass spectrometer (7) manufactured by Baltzers (model QMG 311) and the experimental set-up is shown in the FIG. 6. It is most important that the off-gas be analyzed before the pump (5), since some compounds in the off-gas can be absorbed in the pump oil or in the pump filter. With this experimental set-up it is possible to obtain an oxygen content of 0.01% oxygen in the gas mixture.

The sulphur content in the samples was analyzed using a Leco S-analyzer, model S-132, and the other parameters were analyzed using a Leco Mac 400 (Table II).

TABLE II

Chemical Analysis of Selected Coal Samples

| Coal | Fixed Carbon %* | Volatile matter % | Ash-content % | S-total % |
|---|---|---|---|---|
| Anthracite (An) | 94.5 | 5.5 | 25.20 | 0.61 ± 0.01 |
| SemiAnthracite (Semi An) | 88.6 | 11.4 | 1.02 | 1.74 ± 0.03 |
| Medium volatile bituminous (Mvb) | 71.6 | 28.4 | 13.60 | 0.69 ± 0.01 |
| High volatile bituminous B coal (HvBb I) | 63.8 | 36.2 | 10.40 | 1.16 ± 0.02 |
| High volatile bituminous B coal (HvBb II) | 60.2 | 39.8 | 7.80 | 3.25 ± 0.06 |
| Subbituminous B coal (Sub B) | 45.5 | 54.5 | 5.70 | 0.58 ± 0.01 |
| Peat | 31.9 | 68.1 | 7.80 | 0.40 ± 0.01 |

*These values have been recalculated on a dry and mineral matter free basis

In order to establish the conditions in which $SO_2$ was formed, the $SO_2$ was analyzed continuously during the entire ashing periods. After each ashing the ash was once more analyzed with regard to sulphur content. The sulphur content in the ash was recalculated with regard to the original sulphur content (Table III). It can be seen from Table III that the sulphur losses decrease with increasing helium content (low oxygen content) in the ashing atmosphere.

Consequently it was established that at conditions in which sulphur was 100% recovered in the ash no $SO_2$ was observed in the off-gas.

TABLE III

The relation between the ashing atmosphere and loss of sulphur during ashing for the selected coal samples

| | Sulphur remaining in % after ashing of original sulphur content | | | | | | |
|---|---|---|---|---|---|---|---|
| Atmosphere | An | SemiAn | Mvb | HvBb I | HvBb II | Sub B | Peat |
| 100%O2 | 48.0 | 16.0 | 46.0 | 40.0 | 50.0 | 83.0 | 80.0 |
| 90%O2 10%He | | | 52.0 | | | | |
| 75%O2 25%He | | | 60.0 | | | | |
| 50%O2 50%He | | | 61.0 | | | | |
| 25%O2 75%He | | | 64.0 | | | | |
| 10%O2 90%He | 55.0 | 33.0 | 80.0 | 50.0 | 60.0 | 94.0 | 90.0 |
| 5%O2 95%He | 68.0 | 97.0 | 86.0 | 68.0 | 68.0 | 100.0 | 100.0 |
| 1%O2 99%He | 96.0 | 99.0 | 100.0 | 91.0 | 79.0 | | |
| 0.5%O2 99.5%He | | | | 100.0 | | | |

TABLE III-continued

The relation between the ashing atmosphere and loss of sulphur during ashing for the selected coal samples

| | Sulphur remaining in % after ashing of original sulphur content | | | | | | |
|---|---|---|---|---|---|---|---|
| Atmosphere | An | SemiAn | Mvb | HvBb I | HvBb II | Sub B | Peat |
| 0.1%O2 99.9%He | 100.0 | 100.0 | | | 100.0 | | |

It has been seen experimentally that a low oxygen content in the ashing atmosphere causes a low ashing rate. Since a large number of samples usually needs to be analyzed, it is important to retain as high concentration of oxygen in the atmosphere as possible without any risk of modification or loss of the minerals. A high oxygen content in the ashing atmosphere implies a high risk of oxidizing the sulphides as well as increasing the ashing temperature.

The invention refers also, to obtaining an ashing or a selective oxidation of fuel samples performed in a optimum way, as quickly as possible, without any phase modification of the mineral matter in the sample. Such an ashing can be performed according to FIG. 7. FIG. 7 shows the experimental set-up for an automated VLTA with an IR-detector (14) and a computer (15).

The ashing temperature is measured with an IR-detector (14) placed just outside the vacuum chambers (1), adjacent to a window which permits the IR-radiation to pass.

The ashing temperature is set beforehand considering the accuracy of the analysis and the rank and the sulphur content of the sample. In order to obtain an ashing without phase modification, a further prerequisite is to continually analyze the off-gas with an appropriate instrument such as a mass spectrometer (7).

By controlling and adjusting the RF-effect and the oxygen content in the ashing atmosphere the ashing temperature can be controlled and the $SO_2$ in the off-gas can be maintained at or close to zero. This adjustment can be performed by a computer (15) and a computer program which can be designed in a appropriate form. This computer controls the ashing processes in such a way that when the ashing temperature is too high or the off-gas contains $SO_2$ the RF-effect or the oxygen content or both must be adjusted.

It has been seen experimentally that the oxygen content should be low at the beginning of an ashing and that it can be increased successively after a period of ashing when the carbon content has decreased in the sample. Hereby the ashing period can be decreased without a deterioration of the selectivity.

What is claimed is:
1. A method of ashing solid fuel or combusted or partly combusted fuel or any organic and inorganic matrix which contains minerals in a furnace with a partial pressure less than atmospheric pressure comprising the steps of providing a mixture of oxygen and helium with a total pressure less than the atmospheric pressure and producing a plasma in which the mineral components in the samples are not being affected essentially, wherein the proportion of the gas mixtures achieve a surface temperature not exceeding 150° C. on the sample.

2. A method of ashing solid fuel or combusted or partly combusted fuel or any organic and inorganic matrix which contains minerals in a furnace with a plasma comprising the step of regulating a proportion between an oxygen and helium mixture by a reduction of oxygen content, wherein the surface temperature shall not exceed 150° C. and the said temperature being controlled during the entire ashing procedure.

3. A method of ashing according to claims 1 and 2, wherein the ashing temperature is between 60°–70° C., which brings about a selective oxidation of the matrix.

4. A method of ashing according to claim 1, wherein gas mixture consists of between 0 and 50% oxygen and between 50 and 100% helium.

5. A method of ashing according to claim 1, wherein the surface temperature of the samples is regulated by the oxygen content in the plasma, which consists of a gas mixture of oxygen and helium.

6. A method of ashing according to claim 1, wherein the $SO_2$ content in the "off-gas" produced during ashing will be regulated by the oxygen content in the plasma, which consists of a gas mixture of oxygen and helium.

7. A method of ashing according to claim 2, wherein the surface temperature is recorded by measurement of IR-radiation from the sample and the oxygen content is reduced automatically when said surface temperature reaches a beforehand defined set value.

8. A method of ashing according to claim 6, wherein the surface temperature is recorded by measurement of the IR-radiation from the surface of the sample.

9. A method of ashing according to claim 1, wherein the proportion between oxygen and helium is regulated by a reduction of oxygen content, said reduction of oxygen occuring so that the surface temperature of the sample does not exceed 150° C. and none or insignificant quantities of $SO_2$ vanish from the sample.

10. A method of ashing according to claim 1 for accomplishment of automatic VLTA, wherein the processes are automatically superintended by a mass spectrometer, an IR-detector and a computer, which analyzes and control the ashing process.

11. A method of ashing according to claim 1, wherein the ashing temperature is measured by thermographic indicators, which are sealed in glass ampoules and placed in said furnace.

12. A method of ashing according to claim 2, wherein the ashing temperature is between 60°–70° C., which brings about a selective oxidation of the matrix.

13. A method of ashing according to claim 3, wherein the $SO_2$ content in the "off-gas" produced during ashing will be regulated by the oxygen content in the plasma, which consists of a gas mixture of oxygen and helium.

14. A method of ashing according to claim 12, wherein the $SO_2$ content in the "off-gas" produced during ashing will be regulated by the oxygen content in the plasma, which consists of a gas mixture of oxygen and helium.

15. A method of ashing according to claim 2, wherein the ashing temperature is measured by thermographic indicators, which are sealed in glass ampoules and placed in said furnace.

* * * * *